United States Patent [19]

Harris et al.

[11] Patent Number: 4,483,856

[45] Date of Patent: Nov. 20, 1984

[54] INSECTICIDAL N-SUBSTITUTED-2-(NITROMETHYLENE)-TETRAHYDRO-2H-1,3-THIAZINES

[75] Inventors: Martin Harris; Derek A. Wood, both of Sittingbourne, England

[73] Assignee: Shell Oil Company, Houston, Tex.

[21] Appl. No.: 478,600

[22] Filed: Mar. 24, 1983

[30] Foreign Application Priority Data

Mar. 26, 1982 [GB] United Kingdom ............... 8209028

[51] Int. Cl.³ .................... A01N 43/86; C07D 279/06
[52] U.S. Cl. ...................................... 424/246; 544/54
[58] Field of Search .......................... 544/54; 424/246

[56] References Cited

U.S. PATENT DOCUMENTS 3,933,809  1/1976  Powell ................................. 544/54
3,985,736 10/1976  Powell et al. ....................... 544/54
4,225,603  9/1980  Tieman ............................... 544/54

Primary Examiner—John M. Ford

[57] ABSTRACT

Insecticidal 2-(nitromethylene)-tetrahydro-2H-1,3-thiazines substituted on the nitrogen atom of the ring by a sulfonyl moiety.

6 Claims, No Drawings

INSECTICIDAL N-SUBSTITUTED-2-(NITROMETHYLENE)-TETRAHYDRO-2H-1,3-THIAZINES

DESCRIPTION OF THE INVENTION

It has been found that useful insecticidal activity is possessed by compounds of the formula:

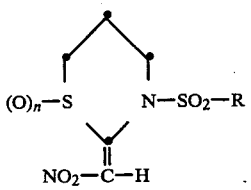

wherein n is zero or 1 and R contains up to twenty carbon atoms and is optionally substituted alkyl.

The alkyl moiety, R, may be either straight-chain or branched-chain in configuration. Suitable substituents include one or more halogen (bromine, chlorine, fluorine, iodine) atoms, alkoxy, alkylcarbonyl, alkoxycarbonyl, alkylcarbonyloxy, oxabicycloalkyl, cycloimido, trialkylsilyl, optionally substituted phenyl and phenoxy, alkenyl, and quaternary ammonium of the formula

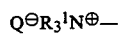

in which each $R^1$ is alkyl and $Q^\ominus$ is a monovalent anion. Suitable substituents on the phenyl and phenoxy moieties include halogen and haloalkyl (bromine, chlorine, fluorine), cyano, nitro, amino, mono- and di-alkylamino, alkyl, alkoxy and alkylthio. In these substituent moieties, each alkyl moiety suitably contains from one to four carbon atoms and is either straight-chain or branched-chain in configuration.

Because of their characteristics, preferred compounds of Formula I are those wherein R is alkyl of from one to twenty carbon atoms, e.g., methyl, ethyl, propyl, butyl, isobutyl, pentyl, methylpentyl, hexyl, heptyl, octyl, nonyl, dodecyl, tetradecyl, hexadecyl or (trimethylbutyl)trimethyloctyl; alkenyl of from two to six carbon atoms, e.g., methylpropenyl; alkyl of from one to four carbon atoms, e.g., methyl, ethyl or propyl, substituted by up to three fluorine, chlorine, bromine or iodine atoms, by alkoxy, alkoxycarbonyl or alkylcarbonyloxy of up to six carbon atoms, e.g., ethoxy, methoxycarbonyl or acetoxy, by oxabicycloalkyl of up to ten carbon atoms, e.g., dimethyl-oxabicycloheptyl, by phthalimido, by phenyl or phenoxy optionally substituted by one or more of halogen (fluorine, chlorine or bromine) and alkyl, alkoxycarbonyl of up to six carbon atoms and trihalomethyl (e.g., methyl, methoxycarbonyl, ethoxycarbonyl and trifluoromethyl), by trialkylsilyl in which each alkyl is of one to six carbon atoms, e.g., trimethylsilyl, or by quaternary ammonium of the formula:

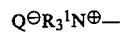

in which each $R^1$ is alkyl of one to six carbon atoms, e.g., ethyl, and $Q^\ominus$ is a halide ion, e.g., chloride, bromide or iodide; and n is zero.

Even more specifically preferred compounds of formula I are those in which R is alkyl of from one to twenty carbon atoms, alkenyl of two to four carbon atoms, haloalkyl of one to four carbon atoms and one to three fluorine, chlorine, bromine or iodine substituents, alkoxyalkyl of two to four carbon atoms, alkoxycarbonylalkyl or alkylcarbonyloxyalkyl of three to five carbon atoms, camphoryl, phthalimidoalkyl in which the alkyl contains from one to four carbon atoms, phenylalkyl in which the alkyl moiety contains from one to four carbon atoms, halobenzyl containing one, two or three chlorine, fluorine or bromine atoms, trifluoromethylbenzyl, methylbenzyl, alkoxycarbonylbenzyl in which the alkoxycarbonyl contains from two to five carbon atoms, halophenoxyalkyl wherein the halogen is chlorine, fluorine or bromine and the alkyl contains from one to four carbon atoms, trimethylsilylalkyl in which the alkyl contains from one to four carbon atoms, or alkyl-trialkyl-ammonium halide wherein each alkyl contains from one to three carbon atoms, and n is zero.

In the alkyl moieties, R, it is preferred that the alpha-carbon atom (that bonded to the sulfur atom) have at least one hydrogen atom bonded thereto; it is even more desirable that it have two hydrogen atoms bonded thereto.

The compounds of Formula I may exist as either of two geometric (cis-trans) isomers, depending upon the spatial configuration about the double bond between the carbon atom of the nitromethylene noiety and the ring carbon atom to which it is bonded. The insecticidal activities of the individual isomers may differ. In the cases of the individual species whose preparation is described in the examples, hereinafter, the isomeric content and configuration of the products have not been ascertained. The invention contemplates all of the insecticidally active isomers, and mixtures thereof, both those which result from the method of synthesis, and those which have been deliberately created.

Compounds of Formula I can be prepared by treating a compound of the formula

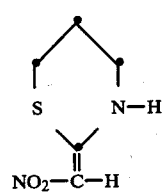

with the appropriate sulfonyl halide, RSO$_2$Hal wherein Hal is bromine or chlorine, in an inert solvent, in an inert atmosphere, and in the presence of a tertiary amine base as hydrogen halide acceptor. Suitable solvents are haloalkanes, such as methylene chloride, and ethers, such as tetrahydrofuran, or dimethylformamide. The reaction proceeds at satisfactory rates at low temperatures, for example, below 0° C., with temperatures of from about −10° C. to about −75° C. being particularly suitable. Suitable amine bases include trimethylamine, triethylamine and ethyldiisopropylamine. Preferably, the reaction is moderated by employing a solution of the sulfonyl halide in the solvent and adding the solution slowly to the stirred solution of the compound of Formula III and the amine. The products are isolated and purified by conventional procedures and techniques.

It may be more convenient to prepare certain of the compounds of Formula I in which R is substituted alkyl by alternative known procedures involving the replacement of one substituent by another. Examples of such replacement reactions are given in Examples 34 and 35 hereinafter, for the replacement of chlorine by iodine, and of iodine by trialkylammonium, respectively.

The compounds of Formula I in which n is one may be prepared by oxidising the corresponding derivative in which n is zero. It may be carried out using conventional oxidising agents, for example peracids such as m-chloroperbenzoic acid or potassium permaganate, or potassium hydrogen persulphate. Conveniently the derivative to be oxidised is dissolved in a suitable solvent, for example a chlorinated hydrocarbon solvent such as chloroform or dichloromethane, or a liquid alkanol such as ethanol.

Compounds of Formula II and their preparation are described in U.S. Pat. No. 3,993,648. The sulfonyl halides, $RSO_2Hal$, are known compounds, many of them being available commercially.

The preparation, isolation and physical properties of typical individual species of the compounds of Formula I, in particular instances, are described in the following examples. In each case, the identity of the product, and each of any intermediate involved, was confirmed by appropriate chemical and spectral analyses.

EXAMPLE 1—N-(Methylsulfonyl)-2-(nitromethylene)-tetrahydro-2H-1,3-thiazine (1)

A solution of 20 g of methanesulfonyl chloride in 150 ml of methylene chloride was added drop-by-drop over a 55 minute period to a stirred mixture of 20 g of 2-(nitromethylene)-tetrahydro-2H-1,3-thiazine and 40 ml of triethylamine in 150 ml of methylene chloride, at $-30°$ C. in a nitrogen atmosphere. The resulting mixture was stirred for 30 minutes at $-30°$ C., and then was washed with 2% hydrochloric acid. The aqueous phase was washed twice with methylene chloride. The resulting organic phases were combined, dried ($Na_2SO_4$), concentrated to about 50 ml, cooled to 0° C., and filtered. The crystalline solid was triturated with cold methylene chloride, to give (1), as a crystalline solid, m.p.: 144°–145° C. (with decomposition).

1 also was prepared as follows:

480 g of 2-nitromethylene-tetrahydro-2H-1,3-thiazine was dissolved in 3 liters of dichloromethane. The solution was cooled to $-70°$ C. and 606 g of triethylamine was added. This solution was stirred at $-65°$ C. to $-70°$ C. under a nitrogen blanket while a solution of 487 g of methylsulphonyl chloride dissolved in dichloromethane was added drop-by-drop over a 6 hour period. A solid containing the desired product precipitated out to form a thick slurry and this was filtered off at $-70°$ C., and dried at ambient temperature. The cake was washed with water to remove the triethylamine hydrochloride, and 1 remained, as a crystalline solid.

EXAMPLE 2—N-(Dodecylsulfonyl)-2-(nitromethylene)-tetrahydro-2H-1,3-thiazine (2)

1.6 g of 1, 3.18 g of ethyldiisopropylamine and 20 ml of methylene chloride were mixed. The mixture was cooled to and stirred at $-60°$ C. under a nitrogen atmosphere while 2.95 g of dodecanesulfonylchloride was added, in portions over a 10 minute period. The mixture was allowed to warm to 10° C. (required 2.5 hours), was stirred at 10° C. for 1 hour, then at 20° C. for 1.5 hours. The resulting mixture was poured into water, the organic phase was separated, dried ($MgSO_4$), filtered and stripped of solvent. The residue, a gum, was chromatographed over silica gel, using methylene chloride as eluent. The product on workup was recrystallized from ethanol to give (2), as a solid, m.p.: 116°–117° C.

EXAMPLE 3—N-(Phenylmethylsulfonyl)-2-(nitromethylene)-tetrahydro-2H-1,3-thiazine (3)

A solution of 2.29 g of phenylmethanesulfonyl chloride in 20 ml of tetrahydrofuran was added drop-by-drop to a stirred slurry of 1.6 g of 1A and 2.02 g of triethylamine in 10 ml of dry tetrahydrofuran at $-50°$ C. The resulting mixture was stirred at $-50°$ C. for 1 hour, when 1.0 g of phenylmethanesulfonyl chloride was added, and the mixture was stirred for a further 1 hour. The mixture was partitioned between methylene chloride and water. The organic phase was separated, washed with water and brine, dried ($MgSO_4$) and stripped of solvent. The residue was flash chromatographed over silica gel, using methylene chloride as eluent, to give (3), as a pale yellow solid, m.p.: 140°–141° C.

EXAMPLES 4 TO 27

The following additional individual species of Formula I were prepared from appropriate starting material according to procedures similar to those described in Examples 1–3. The melting points of these species are set out in Table 1.

TABLE 1

| Example No. | Compound No. | R (Referring to Formula I n = zero) | Melting Point |
| --- | --- | --- | --- |
| 4 | 4 | $CH_3CH_2—$ | 88–89 |
| 5 | 5 | $CH_3CH_2CH_2—$ | 109–110 |
| 6 | 6 | $CH_3(CH_2)_2CH_2—$ | 78–79 |
| 7 | 7 | $CH_3(CH_2)_6CH_2—$ | 104–105 |
| 8 | 8 | $CH_3(CH_2)_{14}CH_2—$ | 114–116 |
| 9 | 9 | $ClCH_2CH_2CH_2—$ | 98–99 |
| 10 | 10 | camphoryl(7,7-dimethyl-2-oxabicyclo[2,2,1]hept-1-ylmethyl | 152–153 |
| 11 | 11 | $CH_3OC(O)(CH_2)_2CH_2—$ | 75–76 |
| 12 | 12 | $CH_3OC(O)CH_2CH_2—$ | 109–110 |
| 13 | 13 | $(CH_3)_2CHCH_2—$ | 109–111 |
| 14 | 14 | $(CH_3)_2CH(CH_2)_2CH_2—$ | 104 |
| 15 | 15 | $CH_3CH_2OCH_2CH_2—$ | 67 |
| 16 | 16 | $CH_3(CH_2)_{12}CH_2—$ | 114 |
| 17 | 17 | $C_6H_5(CH_2)_2CH_2—$ | 41 |
| 18 | 18 | $(CH_3)_3Si(CH_2)_2CH_2—$ | 71 |
| 19 | 19 | $(CH_2=C(CH_3)CH_2—$ | oil |
| 20 | 20 | $4—F—C_6H_4CH_2—$ | — |
| 21 | 21 | phthalimido-$N—CH_2CH_2—$ | 150 |
| 22 | 22 | (trimethylbutyl)trimethyloctyl | — |
| 23 | 23 | $CF_3CH_2—$ | oil |
| 24 | 24 | $CH_3(CH_2)_5CH_2—$ | 112 |
| 25 | 25 | phthalimido-$N—(CH_2)_2CH_2—$ | 133 |
| 26 | 26 | $CH_3C(O)O(CH_2)_2CH_2—$ | 114 |

TABLE 1-continued

| Example No. | Compound No. | R (Referring to Formula I n = zero) | Melting Point |
|---|---|---|---|
| 27 | 27 | 4-Cl—C$_6$H$_4$—O—(CH$_2$)$_2$CH$_2$— | 135 |

EXAMPLE 28—3-(methylsulfonyl)-2-(nitromethylene)-tetrahydro-2H-1,3-thiazine-1-oxide (28)

A solution of 1.56 g of meta-chloroperbenzoic acid in 50 ml of methylene chloride was added over a 5-minute period to a solution of 1.56 g of 1 in 70 ml of methylene chloride at −15° C., under nitrogen. The resulting mixture was stirred at room temperature for one hour, then 5 g of solid sodium carbonate was added. The mixture was stirred for 5 minutes and filtered through sodium carbonate. The solvent was evaporated from the filtrate under reduced pressure, and the residue was recrystallized from methylene chloride to give 28 as a solid, m.p.: 108°–111° C.

EXAMPLE 29

3-(3-chloropropylsulfonyl)-2-(nitromethylene)-tetrahydro-2H-1,3-triazine-1-oxide (29) was prepared as an oil by treating 9 with meta-chloroperbenzoic acid in a manner similar to that described in Example 28.

EXAMPLE 30—3-(2,6-dichlorophenylmethylsulphonyl)-2-(nitromethylene)-tetrahydro-2H-1,3-thiazine (30)

3.2 g of 2-(nitromethylene)-tetrahydro-2H-1,3-thiazine and 5.2 g of N,N-di-isopropylethylamine were dissolved in dimethylformamide. The solution was cooled to −40° to −50° C. and 7.8 g of 2,6-dichlorobenzylsulphonyl chloride was added to it in small portions of about 0.1 g each over a period of one hour. The mixture was allowed to warm to ambient temperature, stirred for a further period of one hour and then poured into 500 ml of an ice/water mixture, to which a few drops of dilute hydrochloric acid had been added. The solid formed was filtered off, washed with water and taken up in dichloromethane. The solution was dried (MgSO$_4$) and the solvent was then removed under reduced pressure. The residue was recrystallised from ethyl acetate to give 30, as a yellow crystalline solid, m.p.: 170° C.

EXAMPLES 31–33

Further individual species of Formula I were prepared from appropriate precursors following procedures similar to those described in Example 30. The species are identified, and their melting points are given in Table 2.

TABLE 2

| Example No. | Compound No. | R (Referring to Formula I, n = zero) | Melting Point (°C.) |
|---|---|---|---|
| 31 | 31 | 2-Cl—C$_6$H$_4$CH$_2$— | 148 |
| 32 | 32 | 3-Cl—C$_6$H$_4$CH$_2$— | 133 |
| 33 | 33 | 2-(C$_2$H$_5$OC(O))C$_6$H$_4$CH$_2$— | 137–138 |

EXAMPLE 34—3-(3-iodopropylsulphonyl)-2-(nitromethylene)-tetrahydro-2H-1,3-thiazine (34)

A mixture of 10 g, of 9, 700 ml of acetone and 17.5 g of sodium iodide was heated under reflux for 16 hours. The solvent was then removed under reduced pressure and the residue was partitioned between water and dichloromethane. The organic phase was dried (MgSO$_4$) and the solvent was then removed under reduced pressure. The residue was recrystallised from dichloromethane to give 34, as a yellow crystalline solid, m.p.: 106°–109° C.

EXAMPLE 35—3-(2-(nitromethylene)-tetrahydro-2H-1,3-thiazin-3-ylsulphonyl)propyl-triethylammonium iodide (35)

4.0 g of 34 and 1.3 g of triethylamine in ethyl acetate were heated under reflux for 53 hours. The reaction mixture was cooled and the precipitate formed was filtered off and recrystallised from ethanol to give 35, as a yellow crystalline solid, m.p.: 150°–157° C.

EXAMPLES 36–43

Further individual species of Formula I were prepared, the species of Examples 36–39 and 43 being prepared by the method of Example 30 and the species of Examples 40–42 being prepared by the method of Example 1. These species are identified, and their melting points are given in Table 3.

TABLE 3

| Example No. | Compound No. | R (Referring to Formula I, n = zero) | Melting Point (°C.) |
|---|---|---|---|
| 36 | 36 | 4-Cl—C$_6$H$_4$CH$_2$— | 144 |
| 37 | 37 | 4-CH$_3$—C$_6$H$_4$CH$_2$— | 155-6 |
| 38 | 38 | 3-(CF$_3$)—C$_6$H$_4$CH$_2$— | 132 |
| 39 | 39 | 4-(CF$_3$)—C$_6$H$_4$CH$_2$— | 152 |
| 40 | 40 | CH$_3$(CH$_2$)$_3$CH$_2$— | 107 |
| 41 | 41 | CH$_3$(CH$_2$)$_3$CH$_2$— | 112 |
| 42 | 42 | CH$_3$(CH$_2$)$_4$CH$_2$— | 101 |
| 43 | 43 | 4-Br—C$_6$H$_4$CH$_2$— | 157-8 |

Compounds of Formula I have been found to possess useful insecticidal activity, and to be comparatively stable to light and oxidation. Compounds of Formula I are of particular interest for control of the larval (caterpillar or "worm") forms of insects of the genus Heliothis, such as H. zea (corn earworm, cotton bollworm, tomato fruitworm), the genus Spodoptera, such as S. littoralis (Egyptian cotton leafworm).

Accordingly, this invention includes a method for controlling insect pests at a locus which comprises applying to the locus an effective amount of at least one compound of Formula I. For such use, the active compound is ordinarily most effectively applied when formulated with a carrier, or a surface-active gent, or both. Therefore, this invention also includes pesticidal compositions which comprise a carrier, or a surfactant or both, together with a pesticidally effective amount of at least one compound of Formula I.

The term "carrier" as used herein means an inert, horticulturally acceptable material (i.e., non-phytotoxic when applied to plants), that may be inorganic or organic and of synthetic or natural origin with which the active compound is mixed or formulated to facilitate its application to the plant, seed, soil and other object to be treated, or is storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example superphosphates.

Suitable liquid carriers include solvents for the compound of this invention and liquids in which the toxicant is insoluble or only slightly soluble.

Examples of such solvents and liquid carriers, generally, are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchlorethylene, trichloroethane, including liquified, normally vaporous, gaseous compounds. Mixtures of different liquids are often suitable.

If used, the surface-active agent may be an emulsifying agent or a dispersing agent or a wetting agent. It may be nonionic, ionic or preferably, mixtures of both. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols; encapsulated formulations and controlled release formulations are also contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10%w of toxicant. Granules may be manufactured by extrusion of plastics, agglomeration or impregnation techniques. Generally, granules will contain 0.5–25%w toxicant and 0–10%w of additives such as stabilizers, slow release modifiers and binding agents. Emulsifiable concentrates usually contain, in addition to the solvent, and when necessary, cosolvent, 10–50%w/v toxicant, 2–20%w/v emulsifiers and 0–20%w/v of appropriate additives such as stabilizers, penetrants and corrosion inhibitors. Suspension concentrations are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, pentrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention can also contain other ingredients, for example, other compounds possessing pesticidal, herbicidal or fungicidal properties, or attractants, such as pheromones, attractive food ingredients, and the like, for use in baits and trap formulations.

The compositions of the invention are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of toxicants of this invention at the locus to be protected—i.e. the applied dosage—is of the order of 0.01% to 0.5% based on the total weight of the formulation, though under some circumstances the effective concentration will be as little as 0.001% or as much as 2%, on the same basis.

Activity of individual species of Formula I with respect to insect pests was determined by using standardized test methods to ascertain the toxicity of the compounds as follows:

EXAMPLE 44

The insecticidal activities of individual species of Formula I were assessed with respect to the Egyptian cotton leafworm (*Spodoptera littoralis*), as follows:

In each test a 0.2% solution or suspension of each test compound in 16.7% acetone in water containing 0.04% Triton X-100 (as surfactant) was used, as were control solutions of water, acetone and Triton X-100 in the same proportions. The tests were all conducted under normal insectary conditions 23° C.±2° C. (fluctuating light and humidity). Each test solution and the control solution was sprayed onto a separate petri dish containing a diet on which the S. littoralis larvae had been reared. When the spray deposit had dried each dish was infested with ten second instar larvae. Mortality assessments were made 1 and 7 days after spraying and the percentage mortality calculated.

In each instance, the toxicity of the compound of the invention was compared to that of a standard pesticide (Parathion), its relative toxicity then being expressed in terms of the relationship between the amount of compound of the invention and the amount of the standard pesticide required to produce the same percentage (50) of mortality in the test insect. By assigning the standard pesticide an arbitrary rating of 100, the toxicities of the compounds of the invention were expressed in terms of the toxicity indices, which compares the toxicity of the compounds of the invention with that of the standard pesticide. That is to say, a test compound having a Toxicity Index of 50 would be half as active, while one having a Toxicity Index of 200 would be twice as active as the standard pesticide. The Toxicity Indices are set forth in Table 4.

TABLE 4

| Compound No. | Toxicity Index | Compound No. | Toxicity Index |
| --- | --- | --- | --- |
| 1 | 150 | 21 | 47 |
| 2 | 110 | 22 | 92 |
| 3 | 130 | 23 | 45 |
| 4 | 92 | 24 | C* |
| 5 | 63 | 25 | 19 |
| 6 | 150 | 26 | 150 |
| 7 | 36 | 27 | 41 |
| 8 | 57 | 28 | 43 |
| 9 | 56 | 29 | 12 |
| 10 | 59 | 30 | 44 |
| 11 | 140 | 31 | 46 |
| 12 | 83 | 32 | 52 |
| 13 | 91 | 33 | 46 |
| 14 | 57 | 34 | 55 |
| 15 | — | 35 | 76 |
| 16 | 120 | 36 | 62 |
| 17 | 16 | 37 | 68 |
| 18 | 34 | 38 | 80 |
| 19 | 41 | 39 | 62 |
| 20 | 52 | 43 | 160 |

*"C" indicates very low mortality, but in the case of Compound 24 the activity is much higher when on-leaf testing is carried out - see the results in Table 5.

EXAMPLE 45

This series of tests illustrates the insecticidal activity of compounds of Formula I by infesting sprayed leaves of chinese cabbage with the larvae of S. littoralis and calculating the toxicity indices in the same manner as the previous example. The test method employed was as follows:

The compounds were prepared for spraying as solutions or suspensions of technical material in 10% aqueous acetone solution, containing 0.025% Triton X-100 as a wetting agent. A range of dilutions of each test compound was sprayed on to a series of petri dishes, each containing a nine-centimeter diameter disc cut from a chinese cabbage leaf. The leaf material was placed with the under-surface uppermost to receive the spray. After being allowed to dry, each dish was infested with 10 foliage-fed, early fourth instar Spodoptera larvae and maintained under laboratory conditions until mortalities were assessed 24 hours later.

The activity in the form of Toxicity Indices for the compounds tested is presented in Table 5.

TABLE 5

| Compound No. | Toxicity Index (mean value) |
| --- | --- |
| 1 | 120 |

TABLE 5-continued

| Compound No. | Toxicity Index (mean value) |
| --- | --- |
| 3 | 130 |
| 11 | 120 |
| 12 | 148 |
| 19 | 110 |
| 21 | 89 |
| 23 | 82 |
| 24 | 176 |
| 26 | 159 |
| 30 | 103 |
| 31 | 114 |
| 32 | 84 |
| 33 | 112 |
| 43 | 92 |

EXAMPLE 46

Corn earworm larvae (*Heliothis zea* (Boddie)) were tested by spraying a broad bean plant with dilutions of acetone solution of test compound into water containing an emulsifier. Immediately after spraying, 5 larvae were transferred to the plant and held for 44–46 hours, at which time the dead and moribund larvae were counted. The tests were conducted employing several different dosage rates for each test compound.

In the cases of Compounds Nos. 1–3, 7, 9, 11, 12, 17, 24, 25, and 35, two replicates were conducted, and the results were expressed in terms of the Toxicity Index in each case. With respect to Compounds Nos. 26, 27, 30–33 and 43, only one replicate was conducted, and the results were expressed in terms of a Preliminary Toxicity Index, which was rounded-off to the nearest multiple of 500.

The results are presented in Table 6.

TABLE 6

| Compound No. | Toxicity Index (*-Preliminary Toxicity Index) |
| --- | --- |
| 1 | 773 |
| 2 | 1311 |
| 3 | 2378 |
| 7 | 365 |
| 9 | 1942 |
| 11 | 1190 |
| 12 | 838 |
| 17 | 1378 |
| 24 | 3012 |
| 25 | 1530 |
| 35 | 1679 |
| 26 | 1500* |
| 27 | 1500* |
| 30 | 2000* |
| 31 | 2000* |
| 32 | 2000* |
| 33 | 1500* |
| 43 | 2000* |

EXAMPLE 47—Persistence

Compounds of Formula I have been tested with respect to their persistence after they were applied to a surface and exposed to light, and have been compared in this respect to, and found to be significantly more persistent than, corresponding N-unsubstituted compounds of U.S. Pat. No. 3,493,648. Compounds of Formula I were found to be more stable to light than were those of the patent.

We claim:

1. A compound of the formula

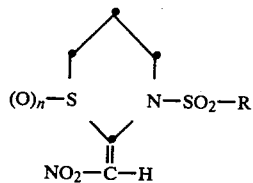

wherein n is zero or one and R is alkyl of from one to twenty carbon atoms; alkenyl of from three to six carbon atoms; alkyl of from one to four carbon atoms substituted by up to three fluorine, chlorine, bromine or iodine atoms, by alkoxy, alkoxycarbonyl or alkylcarbonyloxy of up to six carbon atoms, by oxabicycloalkyl of up to ten carbon atoms, by phthalimido, by phenyl or phenoxy optionally substituted by one or more of halogen, alkyl, alkoxycarbonyl of up to six carbon atoms and trihalomethyl, trialkylsilyl in which each alkyl is of one to six carbon atoms, or by quaternary ammonium of the formula:

$$Q^\ominus R_3^1 N^\oplus -$$

in which each $R^1$ is alkyl of one to six carbon atoms, $Q^\ominus$ is a halide ion, and n is zero.

2. A compound according to claim 1 wherein R is alkyl of from one to 20 carbon atoms, alkenyl of two to four carbon atoms, haloalkyl of one to four carbon atoms and one to three fluorine, chlorine, bromine or iodine substituents, alkoxyalkyl of two to four carbon atoms, alkoxycarbonylalkyl or alkylcarbonyloxyalkyl of three to five carbon atoms, camphoryl, phthalimidoalkyl in which the alkyl contains from one to four carbon atoms, phenylalkyl in which the alkyl moiety contains from one to four carbon atoms, halobenzyl containing one, two or three chlorine, fluorine or bromine atoms, trifluoromethylbenzyl, methylbenzyl, alkoxycarbonylbenzyl in which the alkoxycarbonyl contains from two to five carbon atoms, halophenoxyalkyl wherein the halogen is chlorine, fluorine or bromine and the alkyl contains from one to four carbon atoms, trimethylsilylalkyl in which the alkyl contains from one to four carbon atoms, or alkyl-trialkyl-ammonium halide wherein each alkyl contains from one to three carbon atoms, and n is zero.

3. A compound according to claim 1 wherein the alkyl moiety R has a hydrogen atom bonded to the alpha-carbon atom.

4. A compound according to claim 1 wherein the alpha-carbon atom is bonded to two hydrogen atoms.

5. A method for controlling insects at a locus which comprises applying to said locus an effective amount of a compound of claim 1.

6. A insecticidal composition comprising an effective amount of a compound of claim 1 together with a horticulturally acceptable carrier, and optionally a surface-active agent.

* * * * *